US006599243B2

(12) United States Patent
Woltermann et al.

(10) Patent No.: US 6,599,243 B2
(45) Date of Patent: Jul. 29, 2003

(54) PERSONALIZED DRIVER STRESS PREDICTION USING GEOGRAPHICAL DATABASES

(75) Inventors: Bernd Woltermann, Palo Alto, CA (US); Stefan Schroedl, Palo Alto, CA (US)

(73) Assignee: DaimlerChrysler AG, Stuttgart (DE)

( * ) Notice: Subject to any disclaimer, the term of this patent is extended or adjusted under 35 U.S.C. 154(b) by 0 days.

(21) Appl. No.: 09/989,431

(22) Filed: Nov. 21, 2001

(65) Prior Publication Data

US 2003/0097047 A1 May 22, 2003

(51) Int. Cl.[7] ................................. A61B 5/00
(52) U.S. Cl. ................ 600/300; 600/301; 600/485; 600/500; 600/490; 600/508; 600/549; 340/425.5; 340/435; 340/436; 340/438; 340/903; 701/201; 701/301
(58) Field of Search ................. 600/300, 301, 600/485, 450, 493–6, 500, 508, 549; 701/201, 301; 340/425.5, 435, 436, 438, 460

(56) References Cited

U.S. PATENT DOCUMENTS

| | | | | |
|---|---|---|---|---|
| 5,783,997 A | * | 7/1998 | Saitoh et al. | 340/576 |
| 6,351,698 B1 | * | 2/2002 | Kubota et al. | 701/51 |
| 6,401,029 B1 | * | 6/2002 | Kubota et al. | 701/201 |
| 6,459,365 B2 | * | 10/2002 | Tamura | 340/425.5 |
| 6,501,393 B1 | * | 12/2002 | Richards et al. | 340/993 |

FOREIGN PATENT DOCUMENTS

| | | |
|---|---|---|
| JP | 10082653 | 3/1998 |
| WO | 0157826 | 8/2001 |

OTHER PUBLICATIONS

Wilson, et al., "Position Aware Safety Systems", Daimler-Benz Interim Report, Jul. 20, 1998.
Schroedl, et al., "Mining GPS Traces for Map Refinement", DaimlerChrysler RTNA, May 7, 2001.
Healey, et al., "SmartCar: Detecting Driver Stress" MIT Media Laboratory, 2000.
Rogers, et al., "A Route Advice Agent that Models Driver Preferences", DaimlerChrysler Research and Technology Center.

* cited by examiner

Primary Examiner—Robert L. Nasser
(74) Attorney, Agent, or Firm—Crowell & Moring LLP

(57) ABSTRACT

A system installed in a motor vehicle for inferring a vehicle operator's stress level from body sensors and from environmental data related to the position and operation of the vehicle. The system functions in a training phase using machine learning techniques to derive a model of an individual operators stress reaction to the environment in which the vehicle is operated and, using the results of this training phase, the system is subsequently used to predict stress levels to be expected when certain traffic conditions are imminent based on a projection of the driver's physiolocial state. The result of this prediction of stress level for the individual driver is used to control or warn the driver with respect to operation and scheduling of attention diverting devices such as cellular phones.

14 Claims, 2 Drawing Sheets

PERSONALIZED DRIVER STRESS PREDICTION USING GEOGRAPHICAL DATABASES

BACKGROUND AND SUMMARY OF THE INVENTION

The invention relates to a system for advising or averting potentially dangerous driving situations based on an analysis of driver stress resulting from not only current environmental conditions and current stress levels but also past environmental conditions and previous reactions and stress levels of the driver.

Body sensors and dedicated software packages exist which are able to extract feature vectors during an automobile trip and machine learning techniques have been applied to estimate the driver stress with a target input was derived from a separate inquiry. The capability exist for a system to be installed in an automobile which infers driver stress level from body sensors (blood pressure, ECGEMG, galvanic skin response, respiration, gaze direction, use of pedal and wheel controls etc.). Furthermore, automobiles have digital maps which can be used by an on bullet navigation system for these digital maps maybe enhanced with a variety of attributes, such as traffic control, signs, detail lane intersection structure, traffic flow, etc.

A driver's stress level depends on a variety of determining factors, some of which are beyond the scope of the system (personal situations at home or at work). However, other determining factors correlate to road and traffic conditions which can be retrieved from a digital map (for example, complex intersections, on and off ramps or left turns.) A detailed analysis of such determination of stress level is discussed in "A Route advice Agent that Models Driver Preferences", Seth Rogers, Claude-Nicholas Fiechter, Pat Langley, Third International Conference on Autonomous Agents, Seattle Wash. (1999).

Furthermore, current and future information and entertainment services such as cellular phones, e-mail or news reading applications and radio and navigation system messages require the driver's attention and thus contribute additionally to the stress level.

Although prediction of stress level from body measurement can be accomplished fairly reliably as discussed in "Smart Card: Detecting Driver Stress", Jennifer Healey, Rosalind Pichard, Proceedings ICPR 2000, Barcelona, Spain (2000), the various reactions of drivers under the same external conditions exhibit wide differences.

It is an object of the present invention to provide an individual module which allows for the adaptation of a system on an individual basis.

According to the present invention, a system learns to predict individual driver stress level from features given in a geographical database and from features which indicate current traffic situations. The geographic database provides features such as the current road condition, the type of road (highway, city, etc.), the type of intersection, traffic signs, speed limits, curvature information, and number of lanes. The current traffic situation can be determined by sensors already installed in automobiles for other purposes which can be used to infer features of the current traffic situation. Radar, ESP (Electronic Stability Program), ABS (Antilock Braking System), steering wheel angle, etc. provide information whereby a current traffic situation can be inferred. The outputs of these sensors can be synergistically combined. As an example, with an estimate of a current position with respect to the lanes of the highway obtained from the geographic database, and with optional information concerning turn signals, the system is able to detect lane changes and correlate driving maneuvers with individual stress level. The knowledge as to which lane is occupied by an automobile can be valuable in access the stress potential.

According to the present invention a system is developed which uses previously known machine learning techniques such as neural nets, radial basis functions, etc. to derive a model of the individual driver stress reaction. Subsequently, a learning phase can take place either continually or it can be limited to a dedicated training period. The resulting personal driving model can subsequently be used to predict stress levels in advance by, for example, taking into account approaching intersections, on-ramps, and off-ramps. The system is also able to take advantage of the knowledge of an upcoming route if a driver is following directions from the navigation system.

It is also possible to distinguish between traffic induced stress and a base level stress related to the current personal situation through the continual monitoring of driver stress over a period of time.

As a result of this system, a wide range of possible safety and convenience applications are currently possible. In the future, this system will be able to take advantage of additional information and entertainment services which are related or unrelated to the task of driving. As an example, in addition to the present use of radios and cellular phones, there will be e-mail and news reader services which all require additional attention away from the driving of a vehicle. Therefore, whether these services are used or they are seeking the attention of the driver as by ringing or other indication, they have the ability to contribute to the stress level which can lead to further driver distraction and potential safety risks.

Another aspect of the present invention is the use of current and predicted driver stress levels as an input for a service manager component which will enable or disable services. This allows enhanced information to be provided to the driver only when it is safely possible and the prediction of the stress level of upcoming situations is a determining factor as to whether a driver will be able to handle the diversions caused by these additional services. As an example, services could be either switched on, switched off, or modified, depending on the driver situation. As an example, a cellular phone call could be put on hold while a driver enters an on-ramp.

Another aspect of driver stress which is addressed by the present invention concerns the individualized reaction to particular driving conditions. That is, individual responses to further distractions concerning cellular phones etc. differ from person to person. It is the training aspect of the present invention which allows for direct tracking of the change in stress level after an incoming phone call so that the system can learn the impact caused by such services on the driver in order to improve a safe servicing schedule. In order to accomplish this training, machine learning techniques are applied to associate stress level with attributes of service (e.g. caller ID on cellular phone, category of news) and content-related features (the stock quotes). As a further example, features of the driver's electronic calendar can be input as, for example, a meeting with the boss in the near future which could increase the driver stress level.

With this input and an estimate of the attention level required as well as the duration of various available services, the service manager component of the present invention can not only switch services on or off but control those services to a more sophisticated level (e.g. read e-mail based on priority).

With the present invention, automobile manufacturers and drivers will be able to comply with future safety restrictions or prohibitions on the use of cellular phones in cars. Imposed restrictions will be even more severe for services beyond cellular phones. That is, internet and e-commerce services can be expected to have severe restrictions placed on their use during driving. The present invention may be contemplated as a precondition for delivering additional services to drivers and yet still have all the convenience capabilities within the automobile.

Other objects, advantages and novel features of the present invention will become apparent from the following detailed description of the invention when considered in conjunction with the accompanying drawings.

DETAILED DESCRIPTION OF THE PREFERRED EMBODIMENTS

Figure 1:
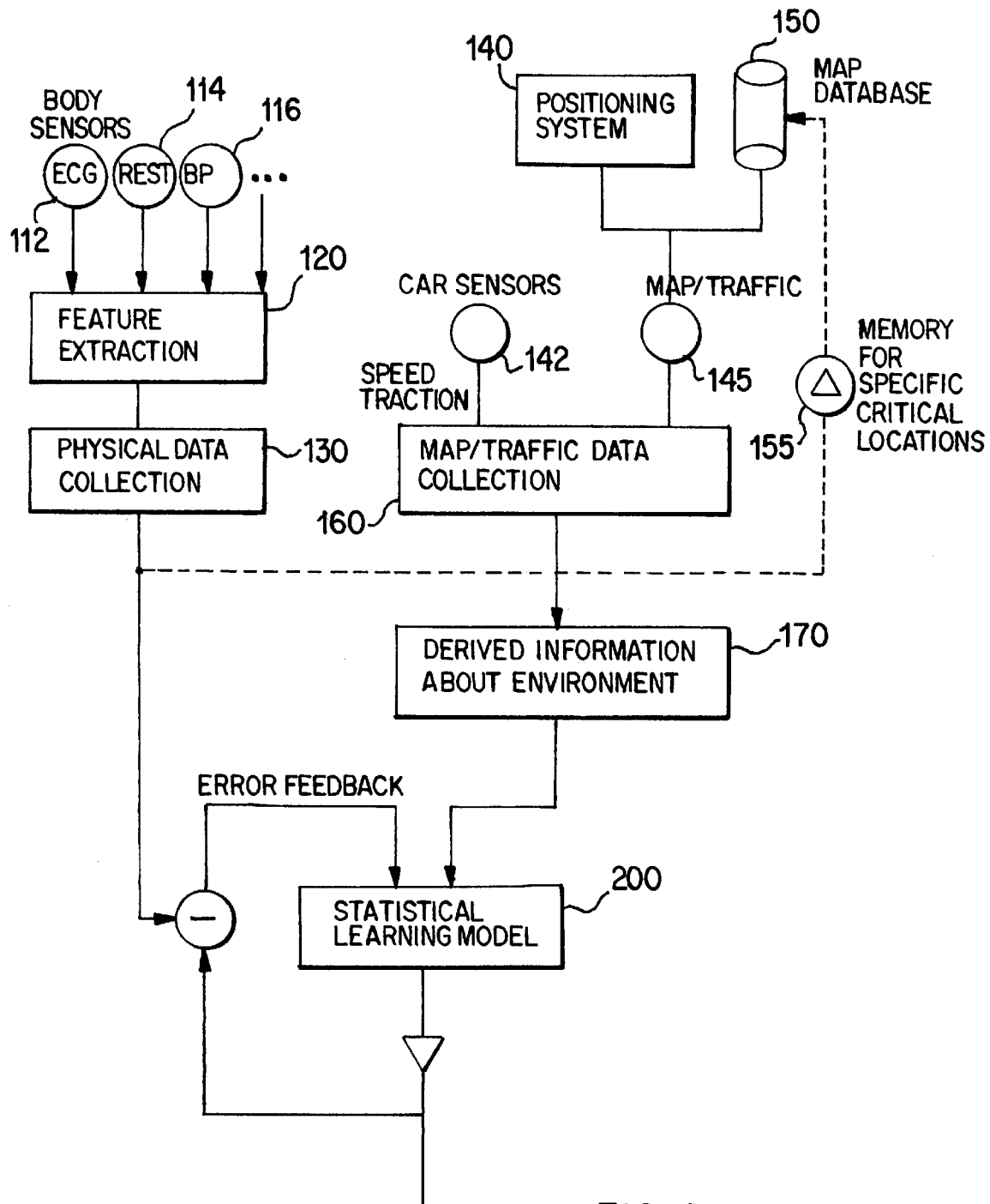
FIG. 1 is a block diagram illustrating the system of the present invention used for the training phase in order to construct the statistical driver model.
Figure 2:
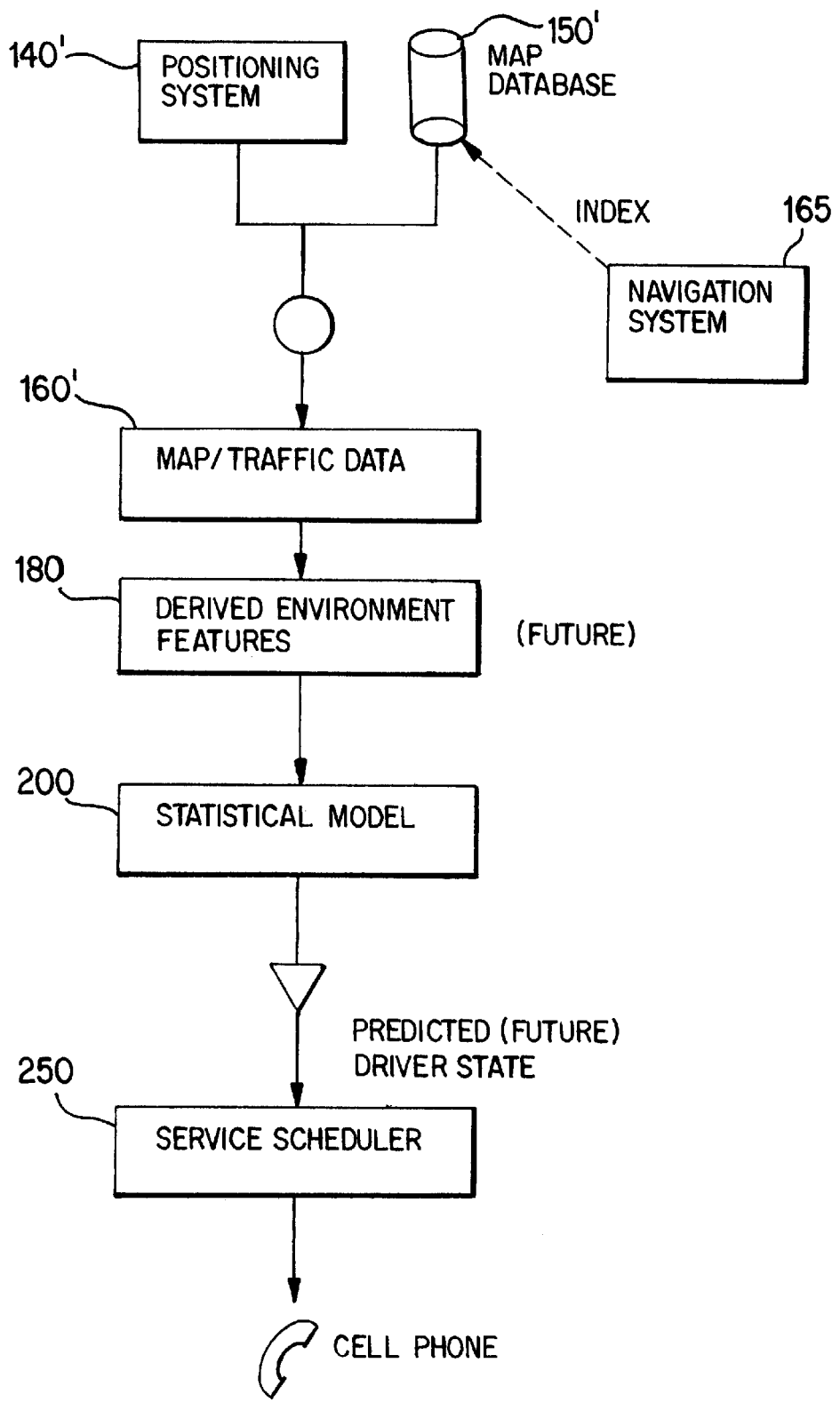
FIG. 2 is a block diagram illustrating the application and prediction phase of the present invention.

The training mode of the system of the present invention is detailed in FIG. 1. An automobile can be equipped with a plurality of body sensors illustrated as electrocardiogram (ECG) 112, a pulse measuring device 114 and a blood pressure monitor 116. Other sets of unobtrusive body sensors, which are preferably contactless, e.g. using infrared sensing devices, can be integrated, for example, into a safety belt or a steering wheel in order to continuously monitor the state of the driver. The outputs of these sensors are fed into the feature extractor 120 to provide particular ranges from the outputs and then to a physical data collector 130 in order to provide monitoring of the physical state of the driver of an automobile with respect to key indicators of stress. Simultaneous with the monitoring of the physical state is a monitoring of the position and environment in which the automobile itself is operating. The positioning system 140, for example a GPS (Global Positioning System), acting in conjunction with a map database 150 provides road features (e.g. position on lane, number of lanes, upcoming intersections) to a collector 145. Additional car sensor information 142 are combined with the collector 145 and are stored in the map/traffic data collector 160. Car sensor 142, which can represent, for example, steering wheel angle, electronic stability program output, ABS, radar, and speed, outputs a signal to the collector 160 to provide a specific traffic data pattern used to derive information concerning the environment 170 at a specific time and specific to the vehicle's operation. The combination of the specific derived environmental information from 170 and the stress level or physical data collection from 130 are used in conjunction with the operation of the statistical learning module 200. The environmental data is input for a statistical module (e.g. a neural net, poynominal or classifier or support vector machine) as statistical learning module 200. The body measurements (i.e. physical data collection) together provide a teaching signal, as shown in the feedback arrangement for the statistical learning module 200. After a training time the system is able to classify whether the driver is relaxed or in a stress mode based upon the physical data collection and the current environmental conditions. After the training phase or mode has been completed by the statistical learning module 200, the entire system switches over to the prediction mode shown in FIG. 2.

In the prediction mode, the statistical module 200, containing driver stress level based upon previous environmental conditions, can now be used to predict a driver's physical state in response to upcoming traffic events. As an example, the system can predict that the blood pressure will rise at the next large intersection if it was previously "earned" in the training mode system. Therefore, given the estimated time to reach a particular intersection, the system is able to warn the driver if he is about to engage in an outside activity such as picking up the phone. Other decisions which could be reached include stopping reading of any news being displayed or the disabling of the phone before the intersection is reached. The prediction system once again uses a positioning system 140' and a map database 150' indexed by a navigation system 165 in order to provide map/traffic data 160' and derived environmental features 180 to be fed to the already "educated" statistical module 200 in order to provide an output which predicts a drivers state in the future for controlling the service schedule 250. The service schedule may include the cellular phone, as discussed above, or an image displayed or any other device which draws the driver's attention away from the road. This control may be in the form of a warning, a temporary disabling or both.

The ability to monitor driver stress continually over time during the training phase makes it possible to distinguish between traffic induced stress and a base level stress related to a current personal situation. While a personal situation is beyond the scope of the system, other situations related to road and traffic conditions, which can be retrieved from the digital map, for example, the complex intersections or the on or off ramps or the left turns, are all factors which can be analyzed.

Because prediction of stress level varies from one individual to another, the present module is constructed specifically to adapt a system individually to each person. Therefore the training phase module provides the necessary background for the functionality between the particular driver stress level and various situations related to traffic conditions, road conditions, location, and speed. The use of machine learning techniques such as neural nets, radial basis functions, etc. to derive a model of the individual stress reaction in the learning phase provides for the unique adaptability of the overall system to a particular individual. Furthermore the system is such that it can take advantage of knowledge of an upcoming route if the driver is following directions from the navigation system 165. In other words, this system offers the ability to know that a stressful situation is approaching so that cautionary procedures in advance can be initiated in terms of either warning or stopping of certain driver distracting functions such a cellular phones, image reading, etc.

Due to the representation in the feature space the system operation is not restricted to previously driven roads, but is also able to generalize the driver stress prediction to map regions not encountered before.

In order to appreciate the operation of this system, a typical example will now be given:

An operator may be assumed to be driving a new Mercedes equipped with the training and prediction of the present invention. The automobile is equipped with a set of unobtrusive body sensors, preferably contactless infrared blood pressure device and other devices integrated into the safety belt and steering wheel for continuous monitoring of the driver's physical state. At the same time, the system is aware of the position and environment of the automobile using a digital map, a positioning system (e.g. high accuracy GPS) and additional car sensors (ABS, ESP, traction control, radar, etc.). The environmental data will be input for a statistical module (e.g., a neural net, polynomial classifier or support vector machine). The body measurements are used as a teaching signal (e.g., the blood pressure as an indicator for stress may rise at large 4-way stop intersections). After a period of training, the system is able to classify whether the driver is relaxed or in a stress mode and can then switch to the prediction mode. Based on events occurring ahead in the route designated by the driver from the navigation system, the invention allows prediction of the driver's physical state in response to upcoming traffic events. As an example, the system will predict that the stress level will rise again at the next large 4-way stop intersection. If, for instance, the estimated time to reach the intersection is two minutes, the system will warn the driver if he is picking up the phone or reading news or disable the phone or the presentation screen for the time before arriving at the intersection.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof

What is claimed is:

1. A system for providing an indication of a vehicle operators stress reaction to a future change in the environment in which said vehicle is being operated; said system comprising:
    at least one sensor for sensing a respective at least one physical parameter of said operator;
    a processing device receiving the outputs of said at least one sensor and providing a training signal;
    a vehicle positioning system for determining a position of said vehicle and outputting a position signal;
    at least one vehicle sensor for determining at least one vehicle operation parameter and outputting at least one vehicle parameter signal;
    a derived environment device having at least one first input receiving respective ones of said at least one vehicle parameter signal and a second input receiving said position signal and providing a vehicle environment output signal;
    a machine statistical learning module having a first input for receiving said vehicle environmental output signal wherein said machine statistical learning module is controlled by said training signal in order to derive a statistical relationship between a physical condition of said operator and an operational environment of said vehicle.

2. A system according to claim 1 wherein said derived environment device further provides an updated vehicle environment signal to said statistical learning module wherein said statistical module compares said updated vehicle environment signal with a stored set of data in said statistical learning module to provide a predicted operator condition output as a function of said updated vehicle environment signal.

3. The system according to claim 2 further comprising a navigation system providing an output to a map database in order to modify said updated vehicle environmental signal on the basis of an anticipated predetermined route to be followed by said vehicle.

4. The system according to claim 1, wherein said at least one sensor for sensing a physical parameter includes at least one of an electrocardiogram measuring device, a pulse measuring device and a blood pressure measuring device.

5. The system according to claim 1, wherein said at least one vehicle sensor includes at least one of a speed measuring device, a traction measuring device, an anti-lock brake measuring device and an electronic stability program.

6. The system according to claim 1, wherein said machine statistical learning module includes one of a neural net, a polynomial classifier and a support vector machine.

7. The system according to claim 1, wherein said at least one sensor for sensing a physical parameter includes an infrared device integrated into the vehicle and proximal to the vehicle operator.

8. The system according to claim 1, wherein said vehicle positioning system includes at least one of a digital map and a global positioning system ("GPS").

9. A system for predicting operator stress during operation of the vehicle, comprising:
    means for sensing physical data related to at least one parameter of said operator;
    means for collecting and arranging said physical data to provide a continuous operator stress condition output signal;
    vehicle positioning means for determining the position of said vehicle;
    vehicle operation means for determining operating characteristics of said vehicle;
    means responsive to an output of said vehicle positioning means and said vehicle operation means in order to provide an environmental information signal concerning said vehicle; and
    a statistical learning device receiving the vehicle environment information signal as an input, wherein said statistical learning device utilizes said continuous operator stress condition output signal as a teaching signal in order to provide a stored statistical learning model relating a physical condition of said operator with the environment of said vehicle.

10. The system according to claim 9, further including a navigation means for indexing said vehicle positioning means to provide an indication of the future environment of said vehicle and outputting a future environment signal as an additional input to said statistical learning device wherein said statistical learning device outputs a future operator stress condition signal.

11. The system according to claim 9, further including a prediction means for providing a predicted stress level and a comparing means for comparing said predicted stress level with an actual stress level provided by said continuous stress condition output signal in order to update said stored statistical learning model.

12. A method for predicting vehicle operator stress reaction to a future change in the environment in which said vehicle is being operated, said method comprising the steps of:
    sensing at least one physical parameter of said operator;
    processing sensed outputs related to said at least one physical parameter and providing a training signal;
    determining a position of said vehicle and outputting a position signal;
    determining at least one vehicle operating parameter and outputting a corresponding at least one vehicle operating parameter signal;

determining a vehicle environment as a function of said at least one vehicle operating parameter signal and said position signal to provide a vehicle environment output signal; and deriving a statistical relationship between a physical condition of said operator and an operational environment of said vehicle as a function of said vehicle environment output signal controlled by said training signal.

13. A method according to claim 12 comprising the further steps of providing an updated vehicle environment signal and comparing said updated vehicle environment signal with a stored set of data concerning said statistical relationship in order to provide a predicted operator condition output as a function of said updated vehicle environment signal.

14. A method according to claim 13 including the further step of supplying a map database in order to modify said updated vehicle environment signal on the basis of an anticipated predetermined route to be followed by said vehicle.

* * * * *